United States Patent [19]

Burg

[11] 4,219,544
[45] Aug. 26, 1980

[54] METHOD FOR TREATING BURNS USING AN EGG YOLK OIL

[76] Inventor: Carol J. Burg, B-10 Moorestown Woods, Moorestown, N.J. 08057

[21] Appl. No.: 15,298

[22] Filed: Feb. 26, 1979

[51] Int. Cl.$^2$ .............................................. A61K 35/48
[52] U.S. Cl. ...................................... 424/105; 424/95; 424/DIG. 13
[58] Field of Search ................... 424/95, DIG. 13, 105

[56] References Cited

U.S. PATENT DOCUMENTS

| | | | |
|---|---|---|---|
| 3,194,732 | 7/1965 | Neuhauser | 424/95 X |
| 3,196,075 | 7/1965 | Neuhauser | 424/95 X |

OTHER PUBLICATIONS

Bandelin et al., J.A.P.A. vol. XIV, No. 2, pp. 106, 107 & 120 (2-1953).
Chemical Abstracts 47:J625 d (1953).
J. Am. Pharm. Assn.-Pharm. Abst., Mar. 1974, p. 84.

*Primary Examiner*—Leonard Schenkman
*Attorney, Agent, or Firm*—Weiser, Stapler & Spivak

[57] ABSTRACT

A method for the treatment of burns such as second and third degree burns to human skin. The method involves the topical application to the burn area of an oil derived from the yolk of an egg such as an avian egg. The raw egg is subjected to a heat treatment whereby the egg yolk oil may be drawn off and used neat or with other pharmaceutically acceptable components.

13 Claims, No Drawings

METHOD FOR TREATING BURNS USING AN EGG YOLK OIL

BACKGROUND OF THE INVENTION

Various portions of the avian egg have found use in pharmaceutical and cosmetic preparations. The albumin, or white, of the egg has been utilized in a pliable bacteriostatic coagulum for the treatment of burns as described in The Lancet, Sept. 18, 1943 issue, at pages 351-353. U.S. Pat Nos. 3,194,732 and 3,196,075 set forth a method of assisting the healing process of abraded, cut or burned human tissue with egg-shell membranes from eggs of domestic fowl.

Ointment preparations using egg oil from a dehydrating azeotropic distillation process are reported in "Pharmaceutical and Cosmetic Application of Egg Oil" by F. J. Bandelin and J. V. Tuschhoff (J. Am. Pharm. Assn., Pract. Pharm. Ed., Vol. XIV, No. 2, p. 106). The distillation process itself is reported in U.S. Pat. No. 2,503,312 and in the article "An Azeotropic Extraction Process for Complete Solvent Rendering Raw Tissues" by E. Levin and F. Lerman (J. Am. Oil Chemists Soc., Oct. 1951, p. 441).

Burns on the human body may be treated by a variety of methods depending on the extent and severity of the burn. Of concern in the therapy is the reduction of the occurance of scar tissue which may remain long after the healing process is complete. An object of the invention in this regard is a burn preparation which allows rapid healing without the formation of permanent scars at the burn site.

SUMMARY OF THE INVENTION

A method for the treatment of burns by the application of a preparation containing egg yolk oil. Preferably the yolk is from an avian egg which has been subjected to a heat treatment. The oil is applied to the burn site and the body's healing of the location is thus allowed to proceed without the formation of permanent scars.

DETAILED DESCRIPTION OF THE INVENTION

The method of the invention involves the treatment of burns, especially burns on human tissue such as skin tissue. In first degree burns, damage is limited to the outer layer of the epidermis with erythema, increased warmth, tenderness and pain and edema, although no vesiculation, usually occurs. In second degree burns, damage extends through the epidermis and into the dermis, but not sufficiently to interfere with rapid regeneration of epithelium. Additionally, vesicles, blebs or bullae will form. Finally, in third degree burns, the epidermis and dermis will be destroyed and the surface may be charred, coagulated or white and lifeless, as from scalds. In deep burns, the wounds may contract and develop into disfiguring or disabling scars.

It has been found that an excellent pharmaceutical preparation for topical application to burn areas, including first-, second- and third-degree areas, of burn victim may be obtained by the processing of egg yolk. The ointment is prepared by deriving from the yolk an oil consisting largely of fats with additional amounts of protein, carbohydrates, ash and water. Avian eggs are preferable in view of their low cost and their ready availability, e.g. eggs from chickens, turkeys or other fowl.

Preferably, the egg yolk oil or ointment is obtained by subjecting the egg yolk to a heat treatment. The heat treatment is preferably carried out on chicken eggs conveniently in two steps. The first heat step is at about 100° C. for a period of at least about five minutes, more preferably for about ten minutes. The first step may be carried out in boiling water whereby maintenance of the desired temperature is assured. In the second step, the solidified egg yolk, preferably separated from the rest of the "hard boiled" egg, is maintained at a temperature and for a time sufficient to release the liquid egg yolk oil components. The second step may be conducted by gently heating the solidified egg yolk over an open flame, being careful not to scorch or char the yolk or the oil drawn off. A review of the chemical analysis of egg oil obtained by the solvent extraction process is set forth in "Pharmaceutical and Cosmetic Applications of Egg Oil" by F. J. Bandelin and J. V. Tuschhoff (J. Am. Pharm. Assn., Prac. Pharm. Ed., Vol. XIV, No. 2, P. 106), which is hereby incorporated by reference. The egg yolk oil may be obtained from the entire egg by a heat treatment but it is most convenient to separate the yolk after it has become solidified.

The egg oil may be used neat on the burn to be treated or may be compounded with pharmaceutically acceptable solvents, fillers, antibacterial agents, thickeners, coloring agents or other conventional ingredients. Preferably, the egg oil preparation is applied at least once a day, more preferably about five times per day, to the burn area with an applicator which allows a gentle application so as not to cause pain.

The preparation of the egg yolk oil product according to an embodiment of the invention and its use in the treatment of burns will be described by the following example.

EXAMPLE 1

Several fresh chicken eggs were maintained at about 100° C. for about five to ten minutes by placement in boiling water. Thereafter, the solidified yolks were removed and held in a dish over an open flame for a time sufficient to cause the release from the yolks of an egg yolk oil, care being exercised to avoid excessive temperatures or burning of the yolks and oil. The effluent egg yolk oil was allowed to cool to room temperature and was analyzed as follows:

| Water | 0.22% |
| --- | --- |
| Protein | 3.53% |
| Fat | 96.1% |
| Carbohydrates | 0.4% |
| Ash (Minerals) | 0.14% |

The above-prepared ointment was used in the treatment of burns as follows.

In Case 1, a seven year old male human subject had a third degree burn on his face as the result of a kerosene explosion. Egg oil prepared according to the invention was applied five times per day for six weeks for a total of about three ounces. Thereafter, the skin returned to normal with no trace of permanent scar tissue.

Case 2 involved a ten month old boy who had third degree chest burns from a fire. After treatment of the area of the burn five times a day for four weeks with the egg oil prepared in Example 1 for a total application of about two ounces, the skin returned to normalcy without the development of scar tissue.

Case 3 involved a two year old male with a second degree burn of the shoulder and the side of the face from boiling water. Treatment with the oil prepared in Example 1 was carried out for four weeks with five applications over the burn area per day for a total of two ounces of egg yolk oil. Recovery from the burn was complete without scar formation.

In Case 4, a 28 year old woman sustained a second degree steam burn of the right forearm. After the application of one ounce of the egg yolk oil prepared in Example 1 over two weeks at a rate of four applications per day, the skin returned to normal with no trace of scar tissue.

In the burn treatment according to the invention, some discoloration may occur although this fades quickly. However, no tightening of the skin in the burn area occurred with the oil treatment.

While the invention has been described by the above specification, it will be appreciated by one skilled in the art that the methods or products of the invention are not limited thereto.

I claim:
1. A method of treating burned tissue comprising topically applying a composition comprising egg yolk oil in a therapeutic amount to alleviate the burn.
2. The method of claim 1, wherein said egg yolk oil is applied in an amount sufficient to cover the burned tissue completely at least once per day.
3. The method of claim 1, wherein said egg yolk oil comprises proteins, fats, carbohydrates, ash and water.
4. The method of claim 1 wherein the composition is applied to human tissue.
5. The method of claim 1 wherein the composition is applied to skin tissue.
6. The method of claim 5 wherein the composition is applied to first-, second- and third-degree burns.
7. The method of claim 1 wherein the composition is an ointment.
8. The method of claim 1 wherein the composition is applied 1 to 5 times per day.
9. The method of claim 8 wherein the composition is applied for four weeks.
10. The method of claim 1 wherein the therapeutic amount is about two ounces.
11. The method of claim 1 wherein the therapeutic amount is about three ounces.
12. A method of treating human burned tissue comprising topically applying egg yolk oil to said tissue in a therapeutic amount to promote healing of the tissue.
13. The method of claim 12 wherein the human burned tissue is skin tissue which had been exposed to first-, second-, and third-degree burns.

* * * * *